United States Patent [19]

Calhoun et al.

[11] Patent Number: 5,606,980
[45] Date of Patent: Mar. 4, 1997

[54] MAGNETIC DEVICE FOR USE WITH MEDICAL CATHETERS AND METHOD

[75] Inventors: Michael W. Calhoun, Fort Lauderdale; Fernando M. Viera, Hialeah, both of Fla.

[73] Assignee: Cordis Corporation, Miami Lakes, Fla.

[21] Appl. No.: 339,376

[22] Filed: Nov. 14, 1994

Related U.S. Application Data

[63] Continuation-in-part of Ser. No. 189,453, Jan. 31, 1994, Pat. No. 5,464,023.

[51] Int. Cl.⁶ ........................................................ A61B 5/00
[52] U.S. Cl. .............................................. 128/772; 128/657
[58] Field of Search ................... 128/657.8; 604/95–96, 604/280.1

[56] References Cited

U.S. PATENT DOCUMENTS

| | | | |
|---|---|---|---|
| 3,749,086 | 7/1973 | Kline et al. | 128/772 |
| 4,244,362 | 1/1981 | Anderson | 128/772 |
| 4,922,923 | 5/1990 | Gambale et al. | 128/772 |
| 4,966,163 | 10/1990 | Kraus et al. | 128/772 |
| 5,113,872 | 5/1992 | Jahrmarkt et al. | 128/772 |
| 5,117,838 | 6/1992 | Palmer et al. | 128/772 |
| 5,133,364 | 7/1992 | Palermo et al. | 128/772 |
| 5,269,759 | 12/1993 | Hernandez et al. | 604/96 |

Primary Examiner—Max Hindenburg
Assistant Examiner—Pamela L. Wingood
Attorney, Agent, or Firm—Michael W. Montgomery

[57] ABSTRACT

A magnetic device for use with a medical catheter and a guidewire incorporates a magnet adapted to attract a portion of the guidewire and thereby impose a magnetic force tending to inhibit longitudinal motion of the guidewire.

18 Claims, 5 Drawing Sheets

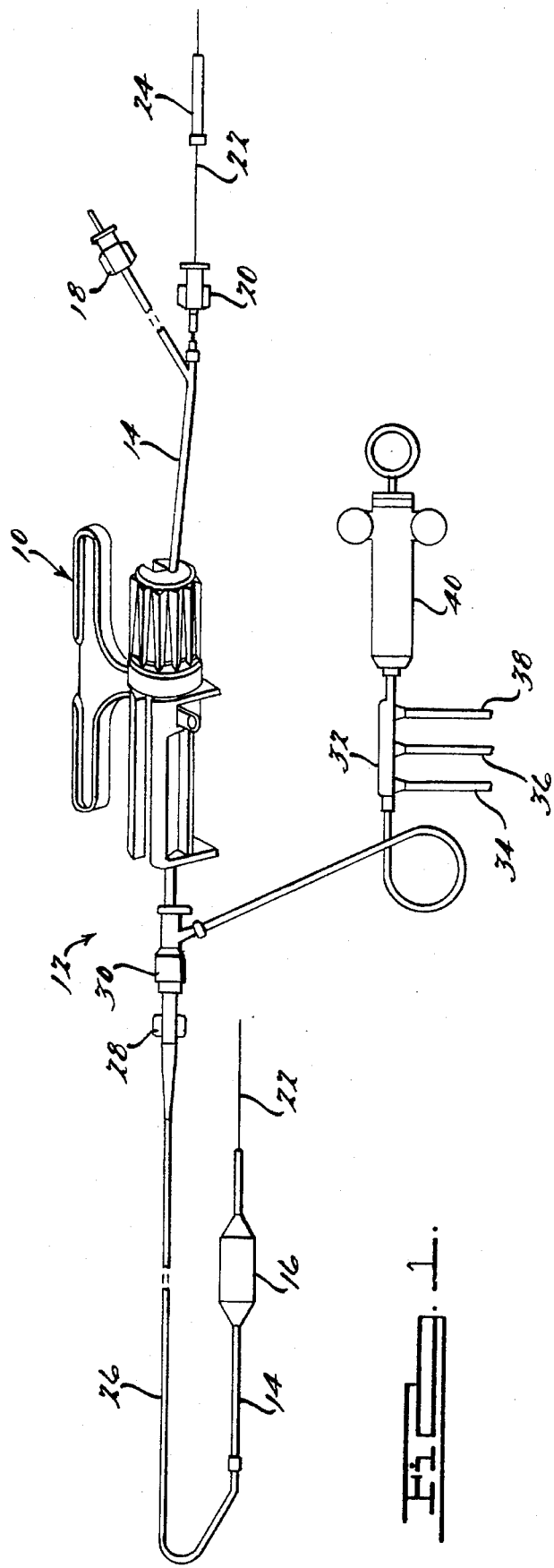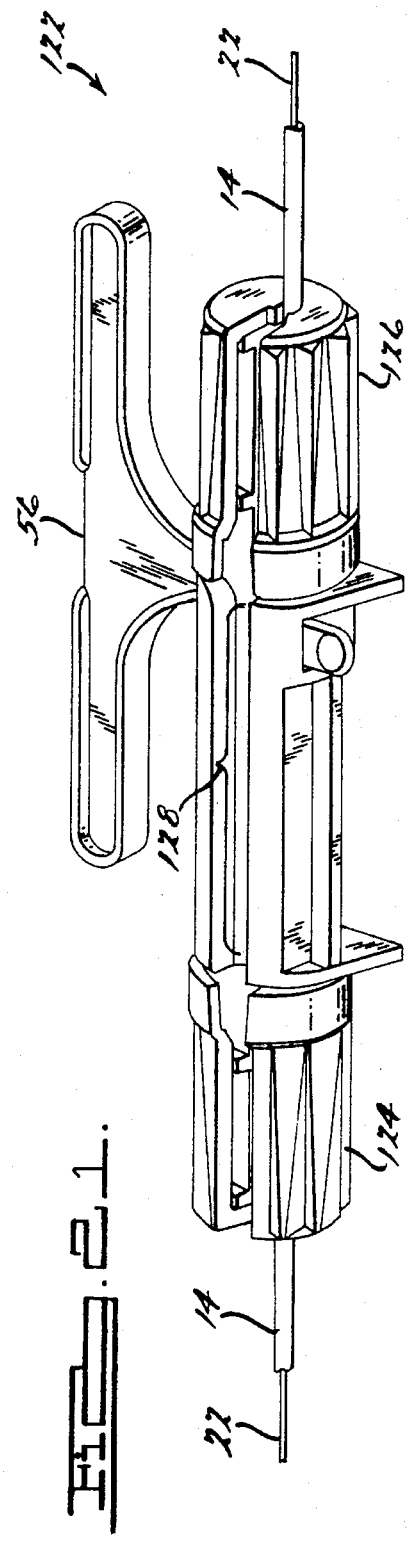

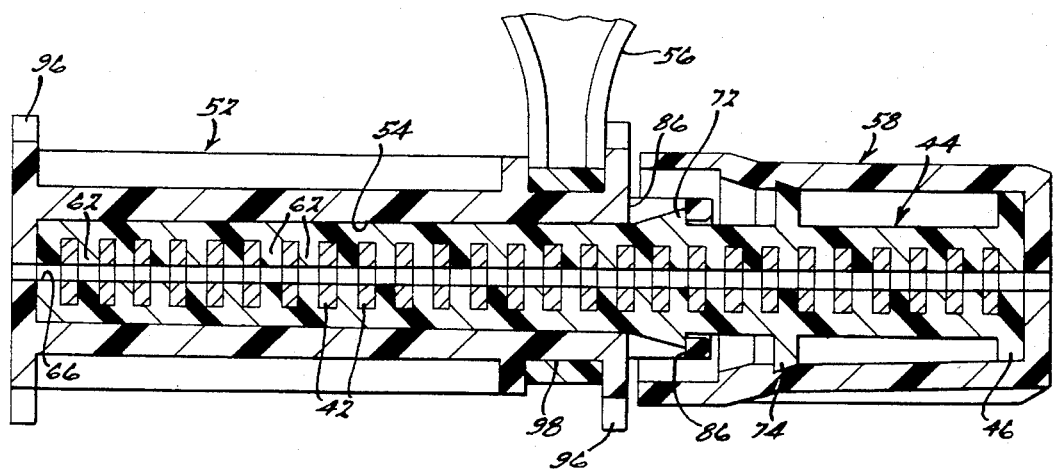
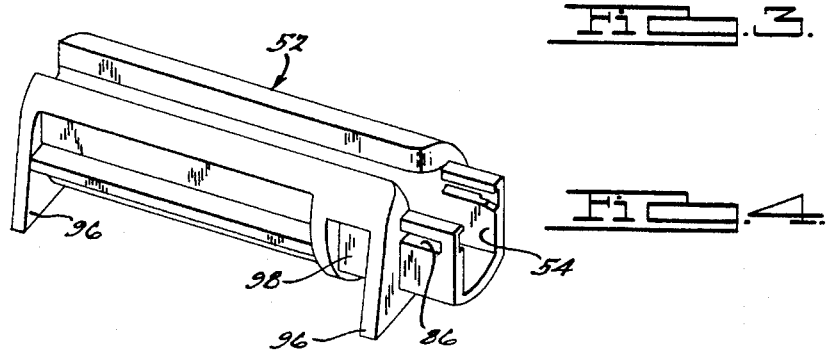
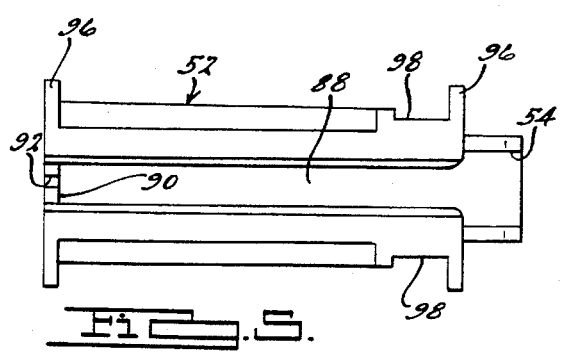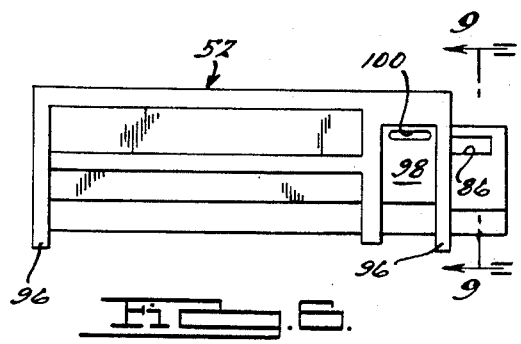
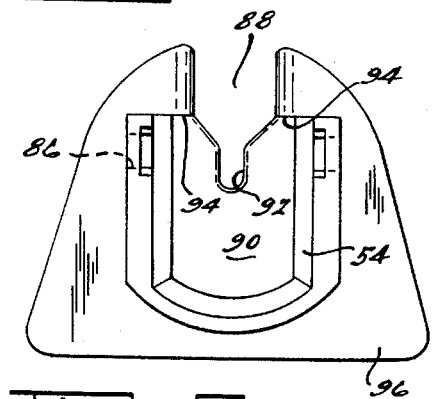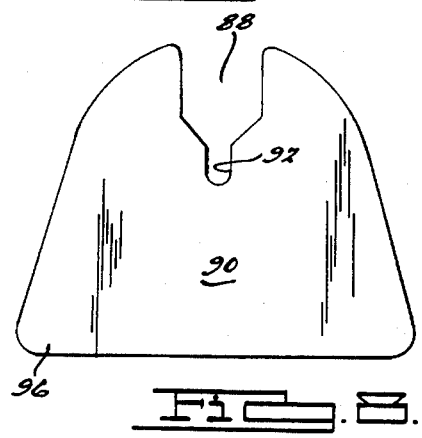

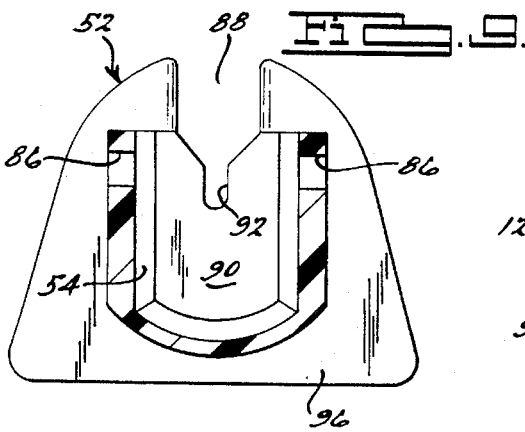
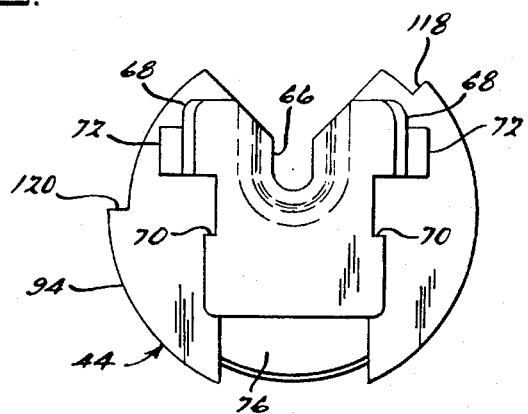
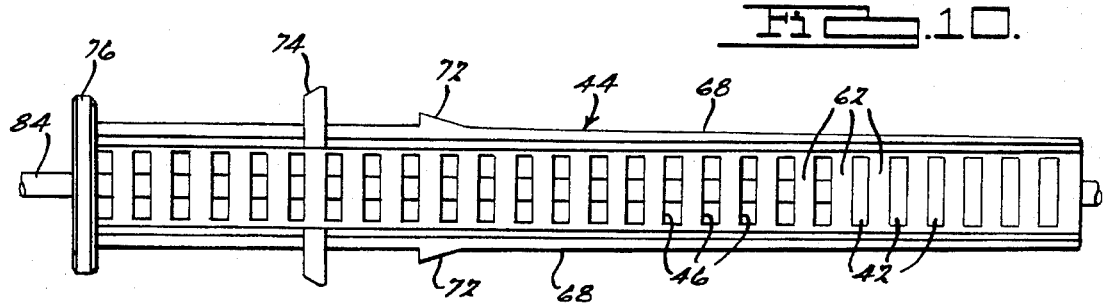
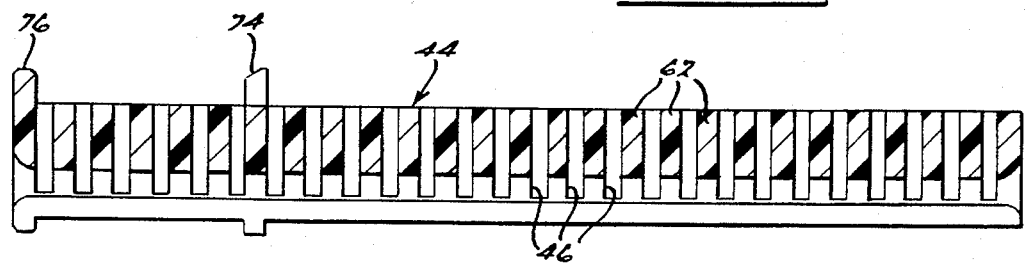
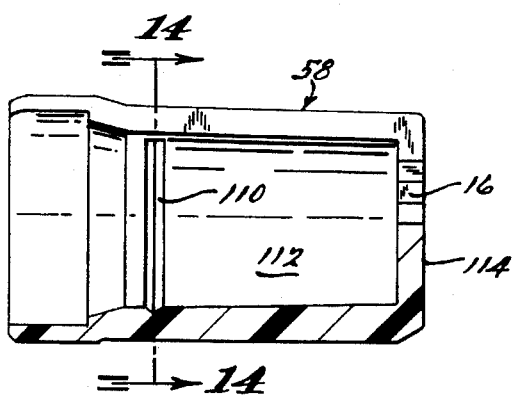
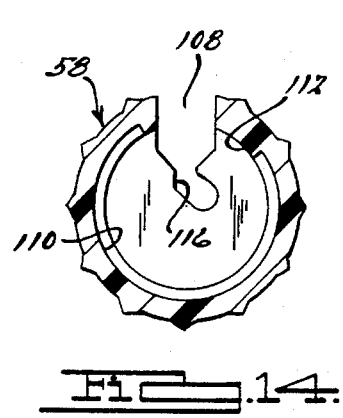

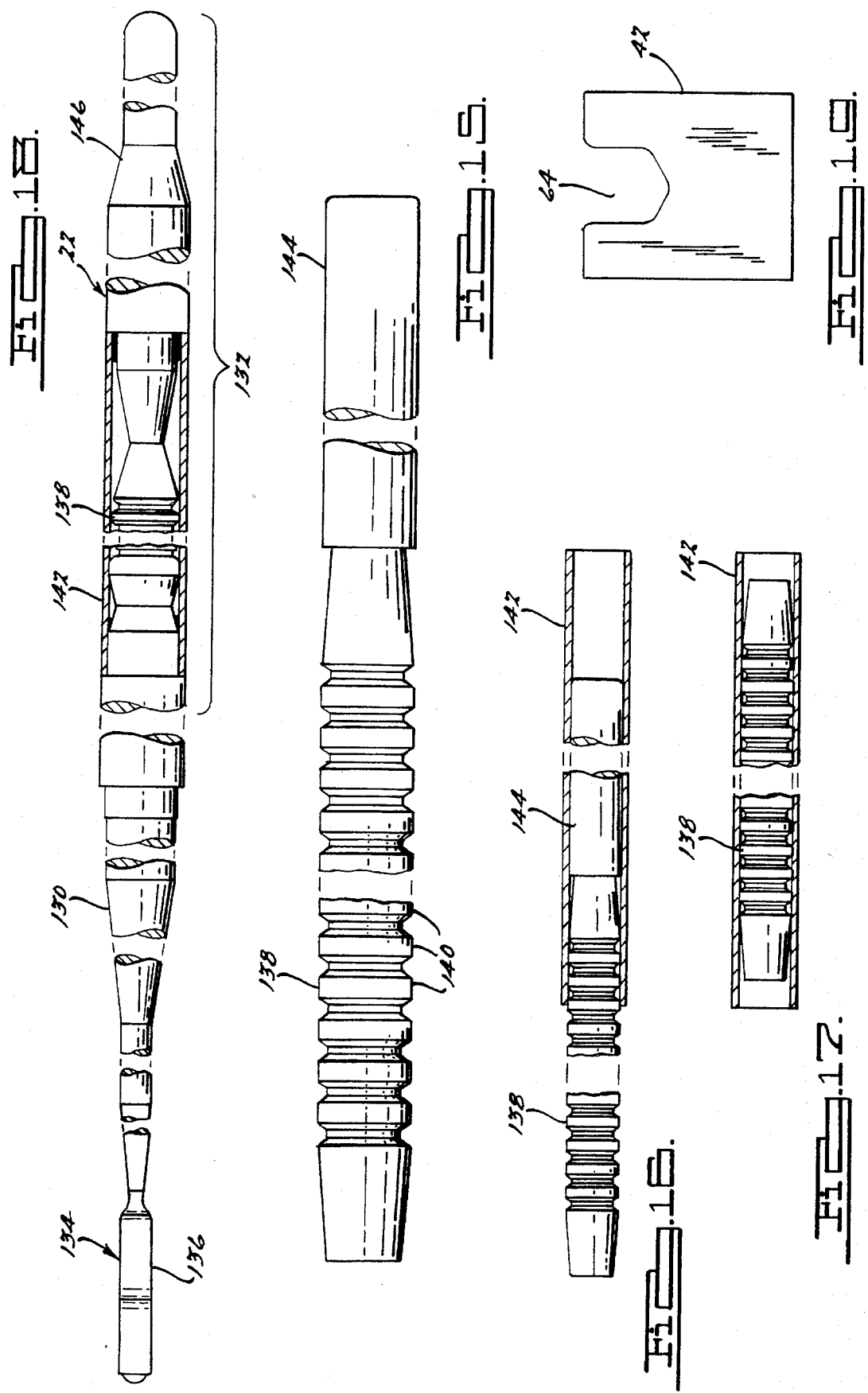

MAGNETIC DEVICE FOR USE WITH MEDICAL CATHETERS AND METHOD

CROSS-REFERENCE TO RELATED APPLICATIONS

This patent application is a continuation-in-part of Ser. No. 08/189,453, filed on Jan. 31, 1994, entitled "Magnetic Exchange Device For Catheters", now U.S. Pat. No. 5,464,023.

BACKGROUND AND DESCRIPTION OF THE INVENTION

The present invention relates generally to medical catheters, and more specifically to a magnetic device and method for facilitating the exchange of catheters during a medical procedure.

Medical catheters of different types are used for a variety of purposes, including coronary angioplasty and angiography. Medical catheters generally have a proximal hub, a body, and a distal tip portion. The body is formed of a flexible, relatively narrow tubular material having sufficient length to traverse a path from an external incision to an internal region of interest within the body of the patient. The proximal hub enables the catheter to be coupled with medical equipment which is used to perform a medical procedure at the distal tip portion.

Many medical catheters are designed for use in conjunction with a guidewire having a distal tip which guides the distal end of the catheter. The guidewire is usually formed of a stainless steel and platinum alloy, and its distal tip is often bent for "steering" the guidewire tip among the body passageways of the patient by twisting the proximal end of the guidewire as it is advanced and retracted. Guidewires are relatively long, usually over 175 centimeters, and preferably approximately 200 centimeters in length. Guidewires are also relatively thin, approximately 0.009 to 0.038 inches in diameter, preferably having a diameter of approximately 0.014 inches. In addition, the distal tip of the core wire is generally much thinner than the balance of the guidewire, on the order of 0.004 inches in diameter.

In a typical medical procedure such as angiography or angioplasty, the catheter is usually preloaded onto the guidewire by feeding the guidewire through the catheter until a relatively short distal portion of guidewire, approximately 1.25 to as long as 10.0 inches, extends distally beyond the tip of the catheter, with a portion of the guidewire extending proximally from the catheter hub. The preloaded catheter and guidewire are then inserted into the body of the patient, steering them into the proper passageways, until the tip of the guidewire is disposed in the desired region. In the alternative, the guidewire may be first inserted within the patient using the "bare wire" technique, and the tubular catheter subsequently inserted by sliding it over the guidewire.

In the particular case of balloon angioplasty, a guiding catheter is initially placed through the femoral artery into the aorta, and its tip is disposed near to the coronary arteries which branch from the aorta, in a region called the ostium. The guiding catheter thus acts as a conduit to access the various coronary arteries with a guidewire and subsequently a balloon catheter. The guiding catheter is constructed of plastic tubing approximately one meter in length, and having a inside diameter substantially within the range of 5 to 9 French size. "French size" is defined as an object having a major diameter of a multiple of 0.013 inches.

Balloon angioplasty catheters and other associated apparatus are described in U.S. Pat. No. 4,906,244, issued on Mar. 6, 1990 to Pinchuk et al., the disclosure of which is incorporated herein by reference. The balloon catheter is an elongated flexible plastic member defining at least two longitudinal passages, or lumens, and preferably having a substantially inelastic balloon located near its distal tip. One lumen accepts the guidewire, while the other lumen allows communication of inflation fluid with the interior of the balloon to inflate it at pressures which usually range from four to twelve atmospheres, to conduct the angioplasty.

The guidewire and balloon catheter assembly is inserted through the guiding catheter until the balloon is near the distal end of the guiding catheter. The balloon catheter is then halted, while the guidewire is advanced from the distal end of the guiding catheter until the distal tip of the guidewire traverses a restricted region of the artery. The guidewire is then held stationary while the balloon catheter is advanced, following the path of the guidewire which is already in place. When the balloon is located in the restricted region, inflation fluid is injected through the inflation lumen, causing the balloon to inflate and reopen the artery to allow sufficient blood flow.

Medical procedures often require the use of different catheters in the same internal region of the body. It often becomes necessary to exchange one catheter for another, and to reposition a distal tip portion of the second catheter in the same location as the first. It is highly desirable to leave the guidewire in place for the duration of the medical procedure, including during the exchange of catheters. If the guidewire is ever removed from the desired position, it must again be steered back to its original position. However, this subsequent navigation may become exceedingly difficult because of the three dimensional complexity of the body passageways. Another reason for maintaining the guidewire in place is that, whenever a foreign object such as the guidewire or a catheter is introduced within a blood vessel, the vessel may spasm and generally constrict along a substantial portion of its length. If the guidewire is removed while the artery is contracted, it may become practically impossible to re-insert the guidewire through the constricted artery.

The problem is that the action of either withdrawing or inserting a catheter over a guidewire imparts a longitudinal force due to friction which tends to dislodge the guidewire. This frictional force between the guidewire and the catheter guidewire lumen is relatively strong, because the difference between the guidewire diameter and the inner diameter of the catheter can be as small as 0.002 inches. Even when the guidewire is provided with a lubricious coating, the guidewire must be restrained from moving relative to the patient. As a result, if the catheter were withdrawn over the proximal end of the guidewire without restraining it, the guidewire would be withdrawn with the removal of the catheter. Accordingly, if a catheter is inserted over a bare wire, the guidewire will tend to be pushed further into the anatomy of the patient.

The reason it is difficult to hold the guidewire stationary is that the majority of the guidewire is inaccessible inside the patient. After the guidewire is in place, the proximal end of the guidewire extends approximately ten inches externally from the body of the patient. At some point during the insertion or withdrawal of a catheter from the guidewire, the entire external portion of the guidewire will be surrounded by the catheter. As a result, neither the internal portion of the guidewire within the body nor the external guidewire portion within the catheter can be conveniently held, to restrain frictional movement of the guidewire with the catheter.

Moreover, the first catheter must be withdrawn entirely from the guidewire before a subsequent catheter may be inserted over the guidewire. Because the full length of the tubular catheter is much longer than the proximal external portion of the guidewire, there is no convenient way to physically anchor the guidewire. As a result, exchanging a first catheter for a second catheter is currently difficult and cumbersome because the relatively inaccessible guidewire must be held stationary.

Previous methods have included the use of an "exchange length" guidewire which is essentially twice the desired length. Such an exchange length guidewire has sufficient length to traverse a path from the point of entry into the patient to a blood vessel stenosis, while providing an external portion which is longer than the full length of the catheter. Such extremely long guidewires are obviously inconvenient and undesirable.

Another method of exchanging catheters provides a removable guidewire extension which is attached to the proximal end of the guidewire, allowing the guidewire to be held in place as the full length of a catheter is removed or inserted, temporarily doubling the length of the guidewire during the exchange. The guidewire length is thus extended such that the proximal end of the guidewire extension can remain proximal from the proximal end of the catheter, even when the catheter is fully threaded onto the guidewire yet entirely external to the patient. An additional assistant is required to manually hold the proximal portion of these extremely long guidewires stationary, preventing guidewire movement during the withdrawal or insertion of the catheter.

The pioneer patent regarding catheter exchange is entitled "Magnetic Guidewire Coupling for Vascular Dilatation Apparatus", U.S. Pat. No. 5,269,759, filed on Jul. 28, 1992, which was issued to Hernandez et al. on Dec. 14, 1993. This patent teaches the concept of utilizing magnetic force to inhibit longitudinal movement of the guidewire relative to the guiding catheter and to the patient, even while a catheter is being withdrawn or inserted over the guidewire. Hernandez discloses a first magnetic clement affixed to the guidewire and a second magnetic clement which is proximate to but external from the guiding catheter to apply a magnetic force to inhibit longitudinal sliding motion of the guidewire within the guiding catheter. The guidewire is therefore magnetically, rather than physically, anchored in a stationary position relative to the patient. Hernandez teaches providing an annular magnet to create a magnetic field in the vicinity of the proximal end of the catheter for magnetically attracting a magnetic portion of the guidewire.

The parent of the present patent application is entitled "Magnetic Exchange Device for Catheter" by Viera, Ser. No. 08/189,453, and was filed on Jan. 31, 1994. Viera teaches a ferromagnetic rod having numerous integral rings, which ;may be affixed to the guidewire and a magnetic retainer having a stack of permanent ring magnets separated by ferromagnetic rings. Viera is able to provide a stronger magnetic field by providing a plurality of magnets.

It is accordingly desirable to provide a magnetic device for facilitating the exchange of medical catheters which provides a strong magnetic resistance against longitudinal slipping of the guidewire in a relatively simple device which occupies a relatively small volume. It is further desirable to provide a magnetic device defining a magnetic channel for removably accepting a portion of a guidewire surrounded by a catheter, which furthers incorporates a mechanical retainer for releasably securing the catheter and guidewire within the magnetic channel, while allowing longitudinal withdrawal and insertion of a catheter.

The unique magnetic device of the present invention provides a magnetic retainer defining a magnetic channel for removably accepting a portion of a guidewire, in which the device imposes a magnetic force on the guidewire which tends to inhibit longitudinal motion of the guidewire with respect to the magnetic device of the present invention.

These and various other objects, advantages and features of the invention will become apparent from the following description and claims, when considered in conjunction with the appended drawings.

BRIEF DESCRIPTION OF THE DRAWINGS

FIG. 1 is a diagrammatic view of a catheter system arranged according to the principles of the present invention;

FIG. 3 is a cross-sectional view of the magnetic device of the present invention;

FIG. 4 is a perspective view of a base, according to the principles of the present invention;

FIG. 5 is a top plan view of the base of FIG. 4;

FIG. 6 is a side elevational view of the base of FIG. 4;

FIGS. 7 and 8 are opposing end elevational views of the base of FIG. 4;

FIG. 9 is a cross-sectional view of the base of FIG. 6, taken along the lines 9—9;

FIG. 10 is an end elevational view of a carrier, according to the principles of the present invention;

FIG. 11 is a bottom plan view of the carrier of FIG. 10;

FIG. 12 is a cross-sectional view of the carrier of FIG. 10;

FIGS. 13 and 14 are cross-sectional views of a locking member, according to the principles of the present invention;

FIG. 15 is a side elevational view of an armature, according to the principles of the present invention;

FIGS. 16 and 17 are cross-sectional views of the armature of FIG. 15 and a protective sleeve, according to the principles of the present invention;

FIG. 18 is a cross-sectional view of a guidewire, according to the principles of the present invention;

FIG. 19 is an elevational view of a magnetic element, according to the present invention; and FIG. 20 is a perspective view of a magnetic device arranged according to the principles of the present invention, in use with a catheter and a guidewire; and FIG. 21 is a perspective view of an alternative embodiment of the present invention.

DETAILED DESCRIPTION OF THE PREFERRED EMBODIMENTS

Figure 2D:
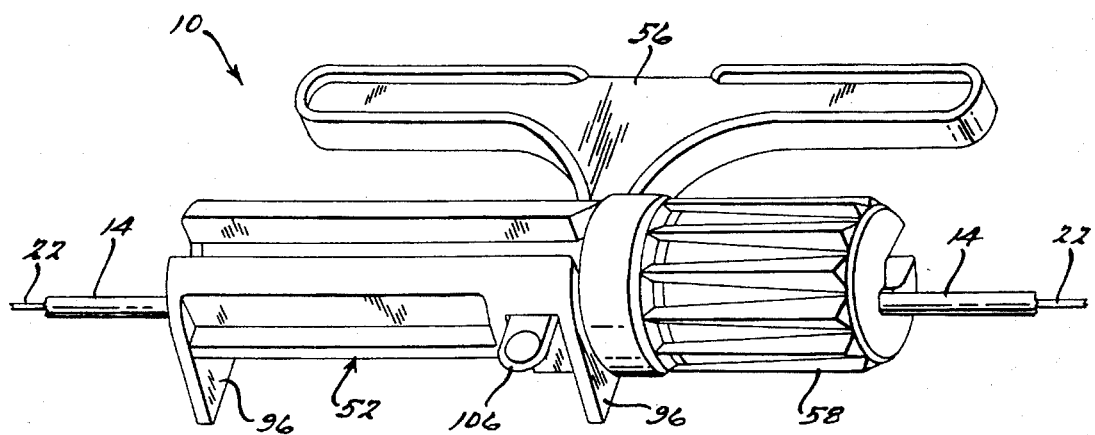
FIG. 2 is an exploded perspective view of the magnetic device of the present invention.

The following description of the preferred embodiments of the present invention is merely illustrative in nature, and as such it does not limit in any way the present invention, its application, or uses. Numerous modifications may be made by those skilled in the an without departing from the true spirit and scope of the invention.

With reference to the drawings, the magnetic device of the present invention is generally designated by reference numeral 10. FIG. 1 shows the magnetic device 10 of the present invention in use with a medical catheter system 12, which may include for example a balloon angioplasty catheter 14 having tubular shaft on which are mounted a distal balloon 16, an inflation hub 18, and a guidewire hub 20, which is threaded over a guidewire 22 having a removable torque handle 24, a guiding catheter 26 having a guiding hub 28, and a hemostatic value 30 connected to a manifold 32 having a pressure tube 34 for monitoring distal blood pressure, an intravenous flush tube 36, and a contrast tube 38 for injecting radiopaque contrast, and a syringe 40.

The guidewire 22 traverses the length of the balloon catheter 14 from the proximal guidewire hub 20 past the distal balloon 16. The inflation hub 18 is coupled with an inflator (not shown) for inflating balloon 16 at high pressure. The syringe 40 and the manifold 32 with its associated tubes 34, 36 and 38 are generally used during a diagnostic angiography which often precedes the angioplasty.

Figure 2:
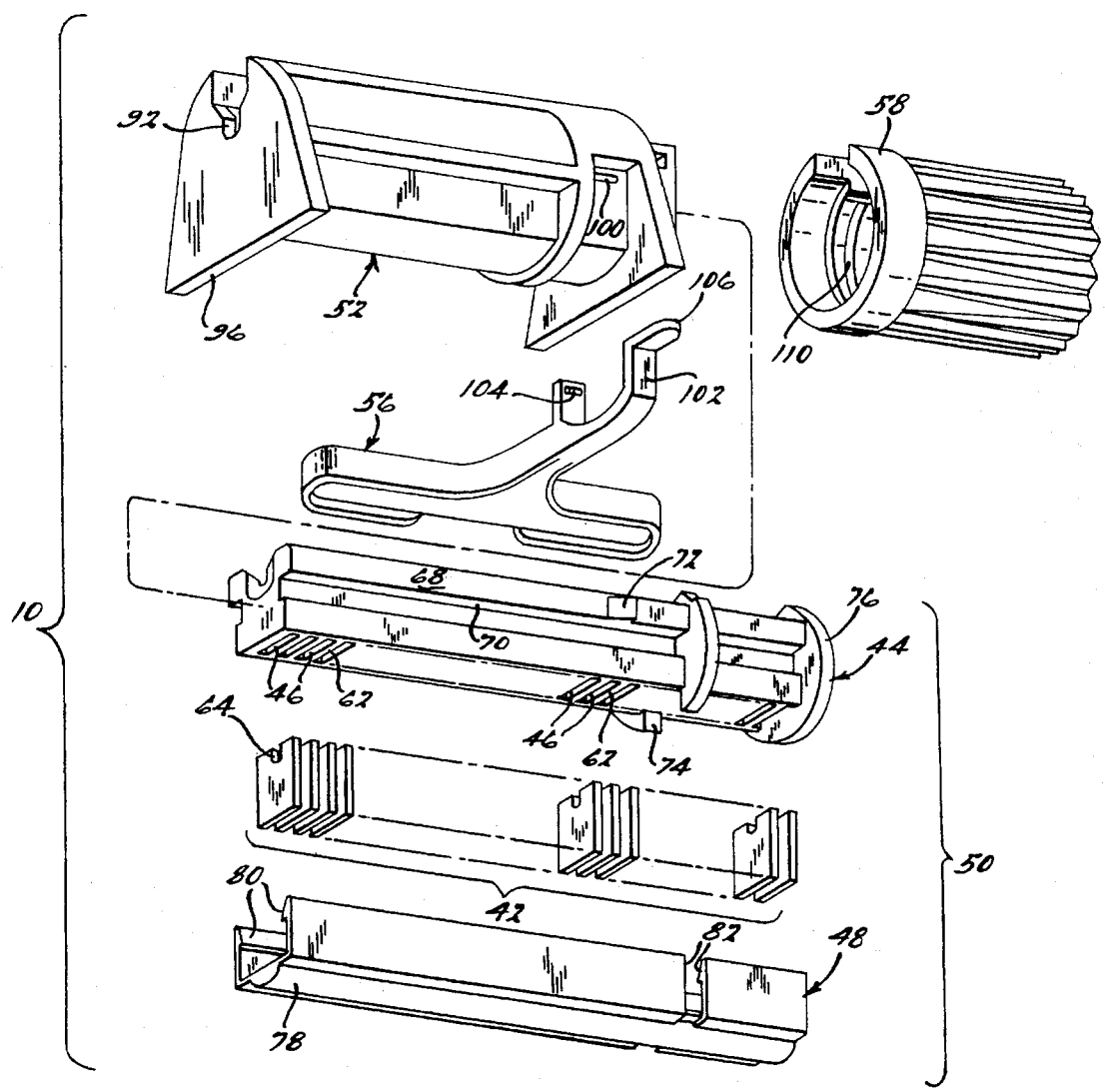

With reference to FIGS. 1 through 3, the novel magnetic device 10 of the present invention provides a unique arrangement of magnetic elements 42 for creating a strong magnetic field which imposes a magnetic force on a portion of a wire such as for example guidewire 22, tending to inhibit longitudinal motion of the wire relative to the magnetic device.

As shown in FIGS. 1-3 and 20, magnetic device 10 preferably includes a number of magnetic elements 42, a carrier member 44 having an equal number of openings or slots 46 for receiving the magnetic elements 42, a cover member 48 for covering the slots 46 to hold the magnetic elements 42 in the carrier member 44, thus forming a carrier subassembly 50, a base member 52 defining a longitudinal base receptacle 54 for accepting the carrier subassembly 50, a removable handle 56 adapted to stabilize the magnetic device 10 on an operating surface, and a locking knob 58 for selectively locking a wire 22 surrounded by a catheter shaft 60 in relative proximity to the magnetic device 10. The term "magnetic element" is used broadly to indicate any object which is capable of creating a magnetic field.

The unique arrangement of the present invention provides a configuration in which the magnetic elements 42 have parallel polarities. In other words, each magnetic element 42 repels the next successive magnet 42. The carrier member 44 is preferably formed of polycarbonate or any other "substantially non-magnetic material", which is defined as a material which cannot be magnetized to create a stronger than negligible magnetic field. A "magnetic material" is defined as a material which is capable of being magnetized, regardless of whether the material is actually magnetized. Likewise, a "magnet" is defined as an object which is currently creating a magnetic field.

Because the magnets 42 are held in a longitudinal array within slots 46 formed in the nonmagnetic carrier 44, the carrier 44 essentially forms a similar array of non-magnetic spacers 62 interspersed between the magnets 42. It should be noted that a simple gap or space between the magnets 42 could also be used without significantly altering the resulting magnetic field. This arrangement of spaced, parallel magnets 42 forms a stronger magnetic field, and a stronger longitudinal magnetic force, than would be produced by an arrangement of similar magnetic elements having alternating polarities, in which each magnet would attract each successive magnet.

The magnetic elements 42 of the present invention are preferably constructed as a series of individual permanent magnets 42, but may also be constructed as a series of electromagnets. The magnetic elements 42 are preferably formed of neodymium-iron-boron, which is a highly ferromagnetic material. Magnets 42 preferably have a flat, thin rectangular shape with a cut-out portion 64, as illustrated in FIGS. 2 and 19. The cut-out portions 64 defined by each of the magnetic elements 42 cooperate with the carrier member 44 to define a longitudinal channel 66 in which the wire 22 may be placed.

The carrier member 44 shown in FIGS. 10-12 defines a plurality of the rectangular slots 46, preferably 25 or more in number, each for accepting one of the magnetic elements 42. The longitudinal channel 66 extends throughout the length of the carrier 44, and matches the cut-out portions 64 formed in each of the magnetic elements 42 when they are in their assembled positions. The carrier 44 and magnets 42 thus provide the desired longitudinal channel 66 which is open in an upward, radial direction, so that the wire 22 may be easily placed in and removed from the channel 66. The carrier 44 is preferably formed so that the entire inner surface of each magnet cut-out portion 64 is exposed. The cut-out portion 64 of each magnet 42 then surrounds a major portion of the radial perimeter of the wire 22. In other words, the magnetic field created by the magnets 42 is not merely adjacent to the wire 22, but rather partially envelops it, creating a stronger longitudinal magnetic force. The carrier 44 further has a pair of matching side rails 68, a pair of shoulder surfaces 70, a pair of ramped anchor projections 72, and a pair of generally annular disk bearings 74 and 76.

The cover member 48 is illustrated in FIG. 2 and is formed as an elongated, generally U-shaped clip having a reinforcing rib 78 and a pair of ramped retaining rails 80. The cover member 48 also has a transverse notch 82 for avoiding interference with the first disk bearing 74.

The magnetic retainer 10 of the present invention is preferably assembled by placing a ferrous rod 84 on a surface (not shown) and dropping the carrier member 44 upside down on top of the rod 84, such that the rod 84 fits within the longitudinal channel 66 defined by the carrier 44. Each of the magnetic elements 42 is then inserted within a successive slot 46 formed in the carrier 44, such that their respective polarities are in arranged in a parallel sequence. Although the magnetic elements 42 would normally repel each other and escape the carrier slots 46, the presence of the ferrous rod 84 causes the magnetic elements 42 to each attract the rod 84. The natural repelling force which is caused when two magnets having parallel polarity are forced into proximity is thus overcome. Several magnets 42 are shown in position within openings 46 in FIG. 11.

After all of the magnetic elements 42 are inserted within their respective slots 46 in the carrier 44, the ferrous rod 84 may be removed from the longitudinal channel 66 of the carrier 44 without disturbing the disposition of the magnets 42. Preferably, the cover or retainer member 48 is snapped onto the underside of the carrier 44 to prevent any of the magnetic elements 42 from escaping, before the ferrous rod 84 is withdrawn from the longitudinal channel 66. The retaining rails 80 on the cover 48 each capture and lock with the shoulder surfaces 70 defined by the carrier 44, thus forming the carrier subassembly or stator 50. The cover member 48 thus covers and holds the magnetic elements 42 in their assembled positions in the carrier 44, preventing them from falling out of the slots 46.

The carrier subassembly or stator 50 is then inserted longitudinally within the longitudinal receptacle 54 defined by the base member 52. The inner surface of receptacle 54 and the width of carrier subassembly 50 are preferably tapered slightly inward, to facilitate insertion of the carrier subassembly 50 within the receptacle 54. When the carrier subassembly 50 is fully inserted within the receptacle 54, the locking anchor projections 62 formed on the carrier 54 snap into an interference fit with a pair of locking apertures 86 formed in the base 52, thus preventing removal of the carrier subassembly 50 from the base 52.

The base member 52 is depicted in FIGS. 4–9, and has a longitudinally extending gap 88, a bulkhead 90 defining a notch 92, a pair of inner shoulder surfaces 94 and a pair of stabilizing legs 96 for encouraging the magnetic device 10 to remain upright on an operating surface. The carrier subassembly 50 is adapted to fit snugly within the inner surfaces of the receptacle 54 after being fully inserted and locked within the base 52. The longitudinal channel 66 defined by the carrier subassembly 50 cooperates with the open gap 88 and the notch 92, thus allowing a wire 22 to be placed within and removed from the magnetic device 10.

The base 52 is further provided with a relieved neck portion 98 and a pair of indentations 100 for cooperating with and accepting a matching clamp portion 102 and protrusions 104 formed on the removable handle 56. The handle 56 may be T-shaped as shown in FIGS. 1 and 2, or may be formed in a variety of other desired shapes. In addition, the handle 56 may be provided with flexible clips (not shown) for clamping the magnetic device 10 onto an object, such as a surgical shroud or drape. The handle 56 should also have a flange 106 which may be depressed to facilitate removal of the handle 56 from the base 52, so that the magnetic device 10 may be more easily held within and manipulated by hand.

The locking knob 58 of the present invention is shown in FIGS. 13 and 14. The locking knob 58 is generally cylindrical, and incorporates a longitudinal gap 108, an annular track 110 formed on the inner surface 112 of the locking knob 58, and an end bulkhead 114 having a notch 116. The gap 108 and notch 116 of the locking knob 58 cooperate with the longitudinal channel 66 of the carrier subassembly 50, as well as the gap 88 and notch 92 of the base 52, to selectively allow a wire 22 to be radially placed within and removed from the present magnetic device 10. The locking knob 58 is inserted over and snaps onto the disc bearings 74 and 76 of the carrier 44, which meet and cooperate with the locking member inner surface 112, to allow the locking knob 58 to rotate about the carrier subassembly 50. The first disc bearing 74 fits within the annular track 110 formed in the locking knob 58, and has stop surfaces 118 and 120 adapted to selectively abut the eccentric ends of the track 110. Because of the eccentric configuration of annular track 110 and stop surfaces 118 and 120, the locking member 58 can be rotated between the offset locking position illustrated in FIGS. 1 and 20 in which a portion of locking member 58 covers a portion of the longitudinal channel 66 to restrict radial removal of the wire 22 from the channel 66, and the aligned releasing position depicted in FIGS. 3, 13 and 14 in which the longitudinal opening 108 of the locking member 58 uncovers that portion of the longitudinal channel 66 to allow radial removal of the wire 22 from the channel 66.

The locking knob 58 is particularly useful because the magnetic field generated collectively by the magnets 42 is strong in a longitudinal direction but relatively weak in a radial direction. The longitudinal force imposed by the preferred embodiment of the present magnetic device 10, having an array of preferably twenty-six magnets 42, can be as strong as approximately 150 grams. On the other hand, the preferred embodiment of a guidewire 22 can be relatively easily removed from the longitudinal channel 56 in a radial direction, especially if the wire 22 is tilted relative to the magnetic device 10. In other words, the magnetic force imposed on the guidewire 22 decays rapidly as it is radially removed from the longitudinal channel 66. The locking knob 58 of the present invention alleviates this problem by selectively locking a portion of the wire 22 within the channel 66 of the magnetic device 10. The notch 116 formed in the end bulkhead 114 of the locking knob 58 is generally similar to the notch 82 of the base 52, except that a radially inner portion of the notch 116 is skewed to accommodate for the passage of a wire 22 and the shaft of a catheter 60 when locking knob 58 is rotated to the locked position shown in FIGS. 1 and 20.

An alternative embodiment of the present invention is illustrated in FIG. 21, in which a modified magnetic device 122 is provided with a first and second locking knob 124 and 126, which are disposed at opposite ends of the device 122 to more completely lock the wire 22 within a longitudinal channel 128. Locking knobs 124 and 126 are preferably torsionally coupled, so that as one knob is rotated from a locked position to a released position, so does the other locking knob.

The magnetic device 10 of the present invention is adapted for use with an improved guidewire 22. Guidewires 22 generally have a distal portion 130 for insertion within the body of a patient and an external portion 132 intended to remain outside of the body. Guidewire 22 is formed similar to that shown in U.S. Pat. No. 4,846,186, entitled "Flexible Guidewire", which was filed on Jan. 12, 1988, the disclosure which is incorporated by reference herein.

The majority of the guidewire 22 is formed as is known in the art, and as such the guidewire 22 is preferably approximately 175 centimeters in length and at most 0.015 inches in diameter. The guidewire 22 incorporates a flexible distal tip 134 in which the core wire is thinner than a remainder of the guidewire 22, and is preferably bent to facilitate steering the guidewire 22. A majority of the guidewire 22 may be provided with a lubricious Teflon® PTFE spray coating, while the tip 134 is preferably surrounded by a flexible coil spring 136.

In order that the external portion 132 of the guidewire 22 will be attracted to the magnetic elements 42 of the magnetic device 10 of the present invention, the guidewire 22 preferably incorporates a ferromagnetic armature 138 formed as shown in FIGS. 15 and 18. The armature 138 is preferably made of vanadium permendur material, also known as Hyperco, but may be formed of any suitable ferromagnetic material. The ferromagnetic material is capable of being magnetized, but preferably has no significant permanent magnetic field. Preferably, the armature 138 has a diameter of 0.0103 inches, and an assembled length of approximately 13.0 inches.

The armature 138 is preferably formed as shown in FIG. 18 of a ferromagnetic material having many nodes 140, each adapted to be attracted by one of the magnetic elements 42. A "node" is defined as any periodic variation in the shape of an object. Each node 140 forms a distinct portion which tends to be attracted more strongly by a magnetic field than the transitions between such portions. Collectively, the nodes 140 have an appearance analogous to an alternating series of stacked dimes and nickels. In other words, each node 140 preferably has a "hockey puck" shape. Dimensionally, each node 140 has a longitudinal length which is equal to the width of a magnetic element 12 plus the distance between that magnet 12 and the next successive magnet 42. The two series of magnetic elements 42 and ferromagnetic nodes 140 therefore have an equivalent repeating periodic length or wavelength.

As a result, when the armature 138 of the wire 22 is placed in proximity to the magnetic array of the present invention, each of the magnetic elements 42 attracts a single node 140 of the armature 138 more strongly than any other node 140 or portion of the armature 138. Indeed, if the respective arrays of magnetic elements 42 and armature nodes 140 are misaligned, the resulting magnetic attraction Will tend to force them to "snap" to the nearest aligned position. Accordingly, if the wire 22 is forced to move in a longitudinal direction with respect to the retainer 10, then the magnetic field of the retainer 10 will tend to again restrict further longitudinal movement from a new, shifted position. In this way, the magnetic device 10 of the present invention will allow only incremental slipping between the wire 22 and retainer 10, as opposed to catastrophically allowing unimpeded longitudinal slipping if the magnetic force is overcome in a particular position.

The guidewire 22 is assembled by initially providing an armature 138 in the configuration shown in FIG. 15, in which a plurality of annular portions of a ferromagnetic wire have been ground away to form the desired nodes 140. There should preferably be a greater number of nodes 140 on the armature 138 than the number of magnetic elements 42 in the magnetic device 10 of the present invention, so that all of the magnets 42 will interact with a corresponding node 140 to produce the full desired longitudinal magnetic force, without laboriously aligning the armature 138 with the magnetic array. It should be noted how difficult such manual alignment would be, for the extent and location of the armature 138 is not obvious in the best of lighting conditions, and many procedures involving guidewires are conducted in darkened operating rooms.

Preferably, the portion of the armature incorporating the nodes 140 is at least 10 inches in length, while each node 140 is preferably 0.150 inches in length, resulting in more than fifty of the nodes 140. The surface of the armature 138 describes an alternating inclined sawtooth pattern, wherein each node 140 is defined by adjacent relatively thick and thin portions.

Because the armature 138 is formed of a ferrous material, it must be isolated from contact with the patient's body or any body fluids. When incorporated within the guidewire 22, the armature must therefore be sealed, preferably with a stainless steel protective sleeve 142 as shown in FIGS. 16 and 17. The sleeve 142 is preferably about 13 inches in length, having an inner diameter of 0.0105 inches and an outer diameter of 0.014 inches. To assemble the armature 138 within the sleeve 142, the armature 138 is placed within the longitudinal channel 66 of a magnetic device 10, where the magnets 42 hold the armature in place while the stainless steel sleeve 142 is forced over the armature as shown in FIG. 16, until the armature 138 is centered within the sleeve 142 as shown in FIG. 17. The ends of the stainless steel sleeve 142 extend approximately 1/16 inch beyond both ends of the armature 138. The armature 138 and stainless steel sleeve 142 are then spot-welded at both ends to the distal portion 130 of the guidewire 22 and to a proximal end portion 146, thus forming the completed guidewire 22 shown in FIG. 18.

The magnetic device 10 of the present invention may be utilized to facilitate the insertion of a catheter 14 over a bare guidewire 22 previously positioned within a patient, without utilizing an extremely long "exchange length" guidewire and without adding a proximal extension, by holding the guidewire 22 near the point of entry and partially feeding the proximal tip of the catheter 14 onto the guidewire 22. This portion of the catheter 14 and guidewire 22 should be placed within the longitudinal channel 66 of the magnetic device 10, and the locking member 58 should then be rotated to the locked position, resulting in the configuration shown in FIGS. 1 and 20. It should be noted that the magnetic device 10 may be used with the locking member 58 arranged either proximal or distal from the remainder of the retainer 10. It is then a simple matter to hold the magnetic retainer 10 in a fixed position relative to the patient while inserting the medical catheter 14 into the body of the patient over the stationary guidewire 22. Holding the magnetic device 10 stationary in turn urges the distal tip 134 of the guidewire 22 to remain in a fixed position relative to the desired interior region of the body.

Alternatively, a catheter 14 may be "pre-loaded", or inserted over the guidewire 22 with the distal end 134 of the guidewire 22 extending past the distal tip of the catheter 14. The resulting assembly is then inserted simultaneously within the body.

After a guidewire 22 and a first catheter 14 have been installed within the patient and after a medical procedure has been performed with the first catheter 14, the magnetic device 10 of the present invention may be used to more easily exchange the first and a second catheter by placing the proximal, external portion of the guidewire 22 and the first catheter 14 within the longitudinal channel 66 of the magnetic device 10. The locking knob 58 is then turned to the locking position to retain the guidewire 22 and first catheter 14 radially within the longitudinal channel 66. After the torque handle 24 is removed from the guidewire 22, the first catheter 14 may then be removed over the guidewire 22 while again restricting longitudinal motion of the guidewire 22 by holding the magnetic retainer 10 stationary. When the first catheter 14 has been fully removed from the guidewire 22, a second catheter may be inserted over the guidewire 22 and through the longitudinal channel 66 of the magnetic device 10 while the magnetic device 10 of the present invention holds the guidewire 22 in a fixed position with respect thereto. Of course, the second catheter and guidewire 22 may be temporarily removed from the magnetic device 10 while performing another medical procedure, subsequently replacing the proximal ends of the second catheter and the guidewire 22 within the longitudinal channel 66 and turning the locking knob 58.

The unique magnetic device of the present invention provides a variety of advantages, including a stronger magnetic field. A removable stabilizing handle is also provided for stabilizing the magnetic device and preventing it from tipping over on an uneven surface, such as the leg of a patient. The handle may be removed for convenience during the exchange of catheters over the guidewire and through the magnetic device. In addition, the locking knob of the present invention prevents the radial removal of a portion of the wire from the longitudinal channel. This feature is important because the magnetic field generated by the magnetic elements is much stronger in a longitudinal direction than a radial direction. In other words, the wire can be peeled from the longitudinal channel with relatively small effort without the presence of a locking member.

It should be understood that an unlimited number of configurations for the present invention can be realized. The foregoing discussion describes merely exemplary embodiments of the principles of the present invention. Those skilled in the art will readily recognize from the description, claims, and drawings that numerous changes and modifications can be made without departing from the spirit and scope of the invention.

We claim:

1. A medical catheter system having a magnetic retainer for use with a medical catheter to impose a magnetic force on a guidewire, comprising:

a plurality of magnetic elements each generating a magnetic field;

a carrier member holding said magnetic elements in a longitudinal array and having a similar array of substantially non-magnetic spacers being interspersed between said magnetic elements;

wherein the respective polarities of said magnetic elements are arranged such that each magnetic element tends to repel the next successive magnetic element; and wherein said magnetic elements are each adapted to attract a proximate one of a plurality of nodes formed on a guidewire, said magnetic retainer allowing longitudinal motion of a medical catheter while imposing a magnetic force tending to inhibit longitudinal motion of said guidewire with respect to said magnetic retainer.

2. The magnetic retainer as set forth in claim 1, further comprising a locking member for selectively securing a portion of said guidewire in proximity to at least one of said magnetic elements.

3. The magnetic retainer as set forth in claim 2, further comprising a second locking member for selectively securing a second portion of said guidewire in proximity to another of said magnetic elements.

4. The magnetic retainer as set forth in claim 1, wherein said magnetic elements are formed as permanent magnets.

5. The magnetic retainer as set forth in claim 1, further comprising a base for stabilizing said magnetic retainer on an operating surface.

6. The magnetic retainer as set forth in claim 5, further comprising a handle which may be removably affixed to said base for further stabilizing the magnetic retainer.

7. The magnetic retainer as set forth in claim 1, further comprising a cover member coupled with said carrier member to restrict removal of said magnetic elements therefrom.

8. The magnetic retainer as set forth in claim 1, wherein said magnetic retainer incorporates a fewer number of said magnetic elements than said nodes defined by said guidewire.

9. The magnetic retainer as set forth in claim 1, wherein said magnetic elements are adapted to attract an alternative one of said nodes when said guidewire is forced to move longitudinally relative to said magnetic retainer, thereby subsequently restricting longitudinal movement of said guidewire from a shifted position.

10. A magnetic retainer for use with a medical catheter to impose a magnetic force on a guidewire, comprising:

a plurality of magnetic elements each generating a magnetic field;

a carrier member holding said magnetic elements in a longitudinal array and having a similar array of substantially non-magnetic spacers interspersed between said magnetic elements;

a longitudinally extending channel defined by said magnetic retainer for accepting a guidewire having a plurality of nodes, said channel being open in a radial direction to allow said guidewire to be removed;

wherein said magnetic elements are each adapted to attract a proximate one of said nodes when said guidewire is placed within said channel, said magnetic retainer thereby allowing longitudinal motion of a medical catheter while imposing a magnetic force tending to inhibit longitudinal motion of said guidewire with respect to said magnetic retainer.

11. The magnetic retainer as set forth in claim 10, further comprising a locking member for selectively securing a portion of said guidewire within said channel.

12. The magnetic retainer as set forth in claim 11, wherein said locking member defines a longitudinal opening, said locking member being rotatably affixed to said carrier for rotation between a first locking position in which a portion of said locking member covers a portion of said channel to restrict radial removal of said guidewire therefrom, and a second releasing position in which said longitudinal opening uncovers said portion of said channel to allow radial removal of said guidewire therefrom.

13. A magnetic device for use with a medical catheter to impose a magnetic force on a guidewire, comprising:

a magnetic element which generates a magnetic field;

a longitudinally extending channel defined by said device for accepting a guidewire, said channel being open in a radial direction; and a locking member for selectively restricting removal of a portion of said guidewire in a radial direction from said channel;

wherein said magnetic element is adapted to attract a portion of said guidewire when said guidewire is placed within said channel, said magnetic device thereby allowing longitudinal motion of a medical catheter while imposing a magnetic force tending to inhibit longitudinal motion of said guidewire with respect to said medical catheter.

14. The magnetic device as set forth in claim 13, further comprising at least one additional magnetic element; a carrier member formed of substantially non-magnetic material and having a longitudinal array of openings, said magnetic elements being disposed within said openings in an arrangement whereby each magnetic element repels the next successive magnetic element; and an armature coupled to said guidewire, said magnetic elements each being adapted to magnetically attract one of a plurality of portions of said armature.

15. The magnetic device as set forth in claim 14, further comprising a sleeve surrounding said armature.

16. A medical catheter system, comprising:

a guidewire adapted to be inserted within a patient;

a tubular medical catheter adapted to be threaded over said guidewire;

a magnetic retainer having a plurality of magnetic elements each generating a magnetic field, a carrier member holding said magnetic elements and having a plurality of substantially non-magnetic spacers interspersed between said magnetic elements, said magnetic retainer defining a channel in which a portion of said catheter and guidewire are disposed, wherein said magnetic elements are each adapted to attract a portion of said guidewire when said guidewire is within said channel, said magnetic retainer thereby allowing longitudinal motion of said medical catheter while imposing a magnetic force tending to inhibit longitudinal motion of said guidewire with respect to said magnetic retainer.

17. The magnetic device as set forth in claim 16, wherein said guidewire further comprises a series of expanded portions having a greater cross-section than a series of reduced portions arranged in an alternating sequence, wherein a sum of the longitudinal dimensions of one of said magnetic elements and an adjacent one of said spacers equals a corresponding sum of the longitudinal dimensions of one of said expanded portions and an adjacent one of said reduced portions.

18. A method of inserting a medical catheter, comprising the steps of:

a) inserting a guidewire within a patient while maintaining a proximal portion of said guidewire outside the patient, said proximal portion defining a plurality of nodes;

b) placing a proximal portion of said guidewire within a longitudinal channel of a magnetic device having a plurality of magnetic elements, each attracting one of said nodes;

c) manipulating a locking member to restrict removal of said guidewire in a radial direction from said channel; and d) inserting a medical catheter over said guidewire, while holding said guidewire in a fixed position relative to said magnetic device by imposing a magnetic force on said guidewire.

* * * * *